United States Patent [19]

Brisson

[11] 4,305,388
[45] Dec. 15, 1981

[54] AUTOMATIC INHALATION TEMPERATURE CONTROL

[75] Inventor: A. Glen Brisson, Schaumburg, Ill.

[73] Assignee: Respiratory Care, Inc., Arlington Heights, Ill.

[21] Appl. No.: 193,838

[22] Filed: Oct. 3, 1980

Related U.S. Application Data

[63] Continuation of Ser. No. 89,320, Filed Oct 30, 1979, now Pat. No. 4,248,217.

[51] Int. Cl.³ .............................................. A61M 16/00
[52] U.S. Cl. ............................. 128/204.17; 128/736; 128/203.27
[58] Field of Search ................. 128/204.17, 203.26, 128/203.27, 203.17, 203.14, 204.21, 204.23, 207.15, 736

[56] References Cited

U.S. PATENT DOCUMENTS

| 3,770,938 | 11/1973 | Agarate | 219/374 |
|---|---|---|---|
| 3,871,371 | 3/1975 | Weigl | 128/204.17 |
| 3,942,515 | 3/1976 | Servos et al. | 128/742 |
| 4,034,740 | 7/1977 | Atherton et al. | 128/1 B |
| 4,121,571 | 10/1978 | Pickering | 128/1 B |
| 4,191,197 | 3/1980 | Benziger | 128/736 |
| 4,263,921 | 4/1981 | Trugillo | 128/736 |

Primary Examiner—Henry J. Recla
Attorney, Agent, or Firm—Eric P. Schellin

[57] ABSTRACT

A system for automatically controlling the amount of heat delivered to a human body through ventilator therapy so as to maintain the body at a desired core temperature. The temperature of the inspired and expired gas is measured by temperature sensors to control operation of an inhalation heater so that the inspired gas temperature tracks the expired gas temperature with different adjusted separations. Automatic switching is under control of a body core temperature sensor detecting deviations from the desired body temperature.

8 Claims, 3 Drawing Figures

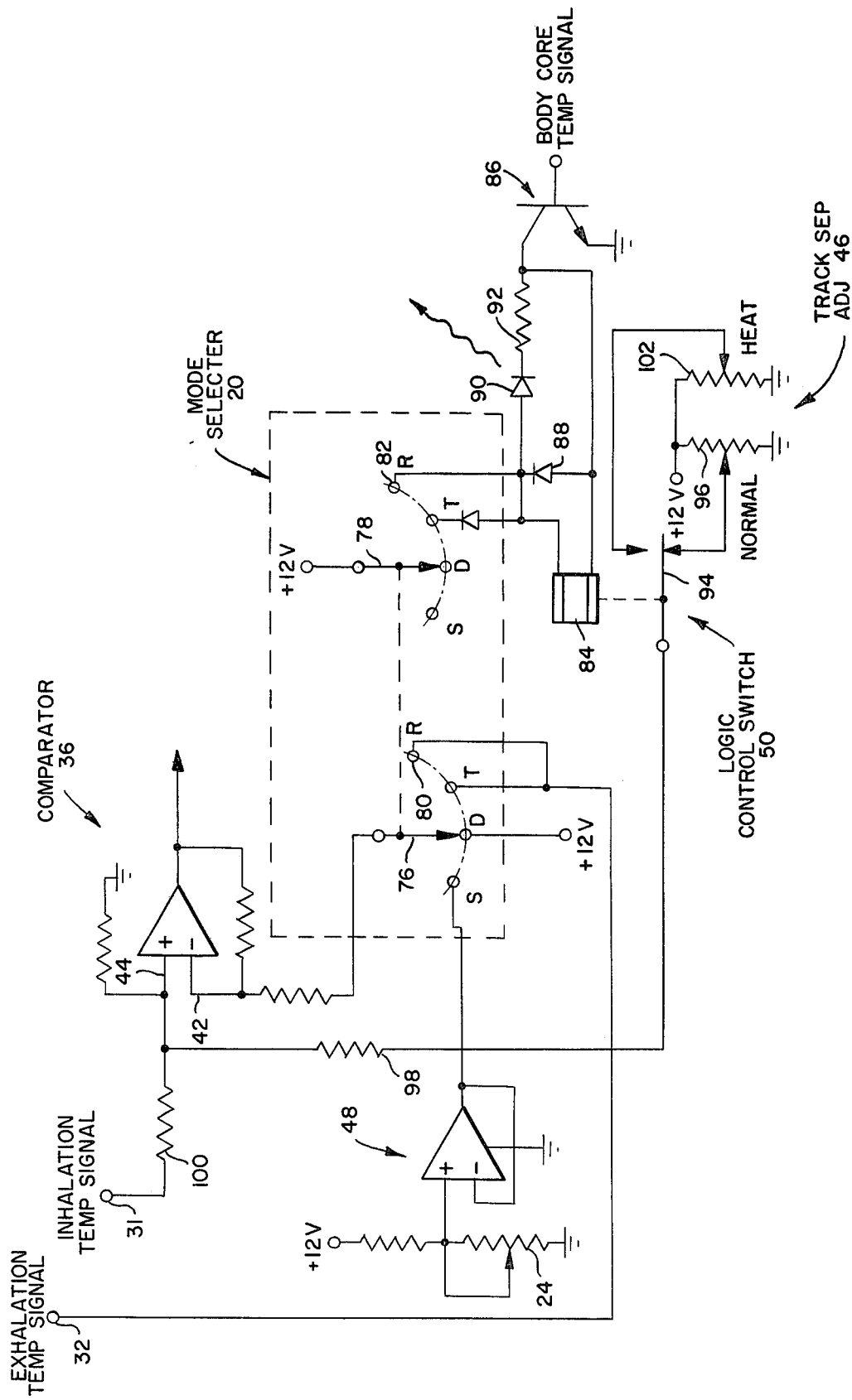

AUTOMATIC INHALATION TEMPERATURE CONTROL

BACKGROUND OF THE INVENTION

This invention relates generally to a ventilator therapy apparatus and method utilizing an inhalation heater and is an improvement over the system disclosed in my prior copending application, Ser. No. 89,320 filed Oct. 30, 1979 now U.S. Pat. No. 4,248,217, with respect to which the present application is a continuation-in-part.

According to the disclosure in my aforementioned prior application, a plural mode type of control system for an inhalation heater is operative only in its tracking mode to so regulate the temperature of the inspired air to track below the temperature of the expired air by a substantially constant amount. The objective of such tracking was to prevent the patient from absorbing heat through the respiratory system in excess amounts that may cause heat stress. Toward that end, temperature sensors were provided for measuring the temperature of both the inspired gas and the expired gas without any direct measurement of body core temperature. Further, in the automatic tracking mode of operation, the inspired gas temperature is tracked only below the expired gas temperature by a substantially constant amount. The foregoing system was based on the heating of the gas by the body after it is inhaled under control of the body's temperature regulating system.

It is well known in the art that during Stage III, Plane III anesthesia, the most common level of anesthesia for major surgery, the body's temperature regulating system is non-functional. Therefore, during long surgical procedures, the patient's body tends to cool down below normal body temperature. This condition can cause serious medical problems in the surgical recovery area and the heater control system disclosed in my prior copending application would not be capable of coping with such a condition.

It is, therefore, an important object of the present invention to provide an improved heater control system for inhalation heaters through which the patient's body temperature may be substantially maintained at a desired level determined by the anesthesiologist despite any malfunction of the body temperature regulatory system of the patient.

SUMMARY OF THE INVENTION

In accordance with the present invention, the inhalation heater control system, as disclosed in my prior copending application aforementioned, is modified by the addition of a body temperature probe and temperature measuring circuit to sense the body core temperature in order to effect automatic switching between tracking below the expired gas temperature and tracking above the expired gas temperature in response to deviation from a desired body temperature. A logic control component therefore receives a temperature signal from a body core temperature measuring component to supply switching signals to an adjustment circuit from which an input is applied to an adjustable comparator to which a second input is applied from the inspired and expired gas temperature sensors in the automatic tracking mode of operation. The heater controlling signal output of the comparator will thereby produce an output signal controlling operation of the inhalation heater as a tracking function of the temperature of the expired gas causing the inspired gas temperature to track below the expired gas temperature by a constant separation amount such as 1° C. or track above the expired gas temperature by another substantially constant separation amount such as 3° C. Automatic switching between such negative and positive tracking functions occurs when the body core temperature drops below or rises above a desired body temperature preset through the body core temperature measuring component. The system will thereby maintain the patient's body core temperature close to the desired level by delivering a controlled amount of heat to the patient through the inhalation heater.

The foregoing automatic switching mode of operation may be effected in a separate operational mode of the inhalation heater control system disclosed in my prior copending application aforementioned, by the addition of the body core temperature measuring component, the logic control switch and the track separation adjustment circuit through which temperature tracking separation may be adjusted for tracking below and above the expired gas temperature.

BRIEF DESCRIPTION OF THE DRAWING FIGURES

FIG. 2 is an electrical circuit diagram showing the improved features of the control system in greater detail.

DETAILED DESCRIPTION OF PREFERRED EMBODIMENT

Figure 1:
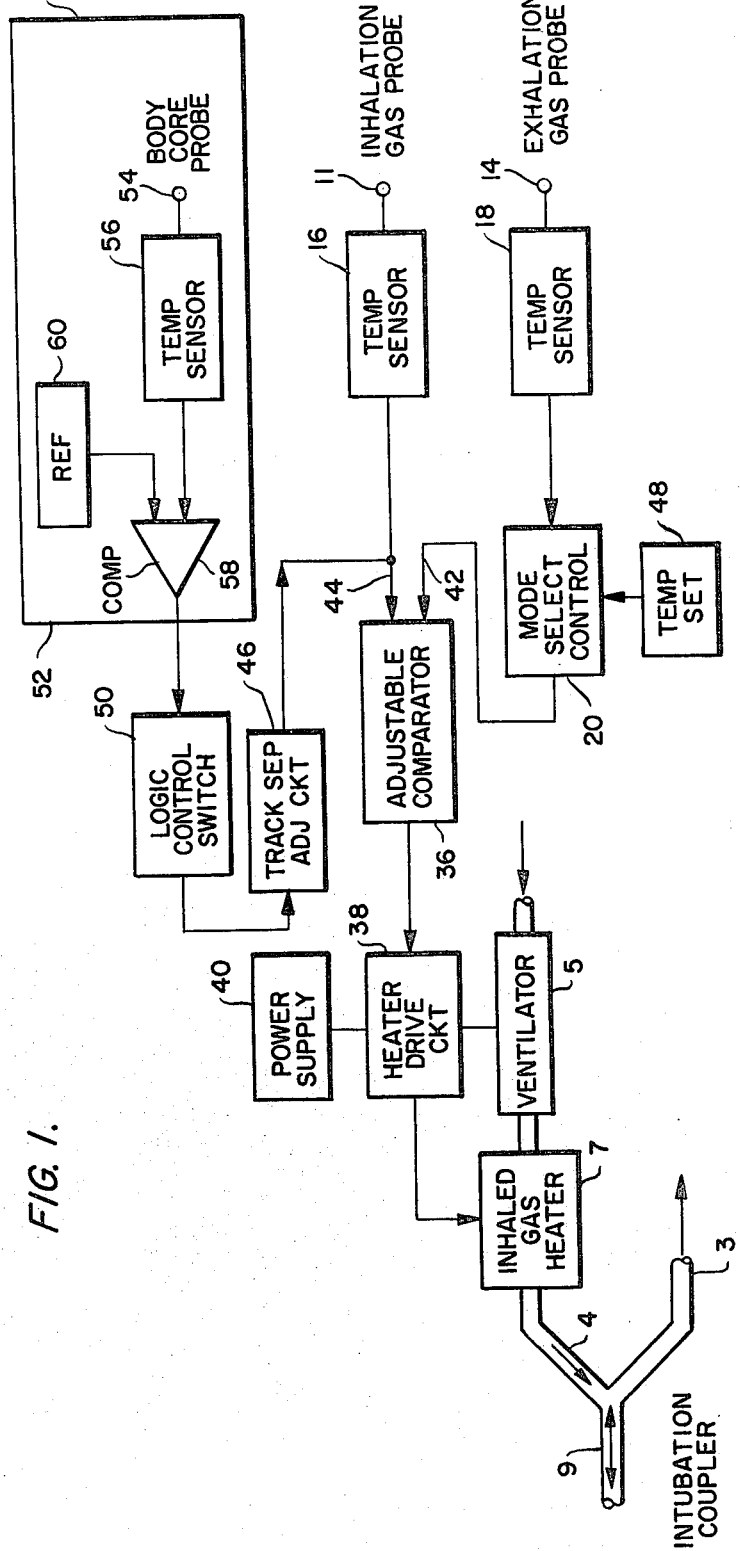
FIG. 1 is a schematic block diagram illustrating the system of the present invention.

Referring now to the drawings in detail, FIG. 1 illustrates a heater control system for an inhalation gas heater 7 associated with a ventilator 5 through which ventilator therapy may be applied to a patient as generally disclosed in my prior copending application aforementioned. Thus, inhaled or inspired gas is conducted through the ventilator 5 to the patient along an inhalation path 4 and through an intubation coupler 9. The intubation coupler is connected to the intubation tube installed within a patient as disclosed in detail in my prior copending application aforementioned. Expired gas is conducted through the coupler 9 to an exhalation path 3. At suitable locations, the temperature of the inhaled and exhaled gas is monitored through gas probes 11 and 14 respectfully connected to temperature sensors 16 and 18 which may be of the electronic thermometer types. The output of the inhalation temperature sensor 16 is fed to one input of adjustable comparator 36, while the output of the exhalation temperature sensor 18 is fed to the other input of the adjustable comparator 36 through a mode selector component 20. The signal output of the comparator 36 is fed through a heater drive circuit 38 isolating the low voltage control portion of the system from a power supply 40. Thus, the power fed from the power supply 40 to the inhalation gas heater 7 for energization thereof will be controlled by the signal received from the comparator 36.

By means of the mode selector component 20, the system may be operated in a set temperature mode. The system is, however, modified within the mode selector component 20 and by the addition of a logic control switch component 50 receiving an input from the output of a generally well known body core temperature measuring component 52 which includes a body probe 54 connected to a temperature sensor 56, the output of which is fed to one input of a comparator 58, the other input of the comparator being connected to a temperature reference 60. The output of the comparator 58 supplies the aforementioned input signal to the logic control switch component 50 in order to effect automatic switching when the body temperature deviates from a desired body temperature level determined through the temperature reference 60. To effect such automatic switching, in accordance with one embodiment of the invention, the signal output of the logic control component 50 operates on the track separation adjustment circuit 46 to change the voltage level applied to the input 44 of the adjustable comparator 36.

Figure 3:
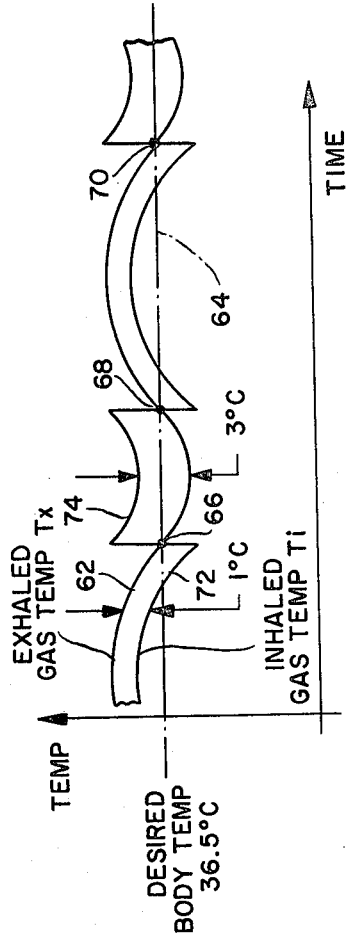
FIG. 3 is a graphical illustration of the operational characteristics associated with the improved system of the present invention.

Referring now to FIG. 3, operation of the track separation control logic is graphically illustrated. When the body core temperature is below the desired value denoted by reference numeral 64, track separation is selected by the logic to bring body temperature up to the desired value. When the desired body temperature is attained, the control logic selects a track separation through the adjustment circuit 46 to cause the inspired gas to track along curve portion 72, 1° C. below the expired gas temperature denoted by curve 62. If the body temperature drops below the desired value again, the control logic will select the 3° C. track separation condition as denoted by curve portion 74 to again force the body temperature up toward the desired value. The expired gas temperature as denoted by curve 62 in FIG. 3 thus provides a reference tracked by the inspired gas temperature along curve portions 72 and 74 which cross curve 62 at separation switching points 66, 68 and 70 in FIG. 3.

FIG. 2 illustrates in greater detail certain portions of the heater control circuit, which is otherwise generally similar to that disclosed in my prior copending application aforementioned. The heater control system is switched to the various operational modes are previously described in my prior copending application aforementioned by displacement of the switch sections 76 and 78 of the mode selector component 20 between its operative positions engaging the various mode contacts. The automatic switching mode of operation is effected when the contactors of the switch sections 76 and 78 engage the contacts 80 and 82. When contact 80 is engaged, the exhalation temperature signal output of the temperature sensor 18 is fed to the input 42 of the comparator 36. Thus, normal negative tracking operation occurs as described in my prior copending application aforementioned. At the same time, the switch section 78 engages a contact 82 which is connected to the logic control switch component 50. Accordingly, voltage is applied through contact 82 to one terminal of relay coil 84 in the logic control switch component, the other terminal of which is connected to the collector of a signal transistor 86 having an input base to which a signal input is applied from the output of the body core temperature component 52. The low voltage source connected to the switch section 78 applies appropriate voltages to the interconnected terminals of the relay coil 84 and collector of transistor 86 in order to maintain the relay coil in one state when the body core temperature signal reflects a body temperature above the desired temperature level and in another operational state when the body core temperature is below the desired temperature level. When the body core temperature is above the desired level, the signal transistor 86 will be switched off and any back EMF from relay coil 84 is absorbed by diode 88. With the relay coil 84 thereby deenergized, its relay switch 94 will be in its normal position engaging one of the relay contacts connected to the normal potentiometer 96 associated with the track separation adjustment circuit 46. An adjusted reference voltage will therefore be applied by potentiometer 96, relay switch 94 and signal line resistor 98 to the input 44 of the comparator 36 to which the inhalation temperature signal is fed through resistor 100 thereby producing an output of the comparator 36 causing the heater to supply a controlled amount of heat to cause inhaled gas temperature to track the expired gas temperature by a substantially constant adjusted amount such as 1° C. as aforementioned. When the body core temperature drops below the desired level 64 because the body's temperature regulating system becomes non-functional, a signal is applied by component 52 to the signal transistor 86 causing it to conduct. A relay energizing circuit is thereby completed through the relay coil 84 in series with a light emitting diode 90 and resistor 92. The LED 90 will then indicate operation of the control logic while the relay switch 94 is displaced to its other operative position engaging its other relay contact to thereby connect the warming potentiometer 102 to the input 44 of the comparator 36 through signal input resistor 98. The comparator 36 will then be operative to cause the inhaled gas temperature to track above the expired gas temperature by an adjusted amount, such as 3° C., determined by the setting of potentiometer 102. A controlled amount of heat is thereby delivered to the patient's body to compensate for heat loss until the body temperature is again at or above desired level 64.

Although the heater 7 is shown in FIG. 1 in the gas line 4 between the patient and ventilator 5, the described system is also applicable to a patient on spontaneous respiration as well as a patient on anesthesia ventilator.

What is claimed is:

1. In a respiratory gas breathing system having an inhalation gas heater, sensor means for measuring inhalation and exhalation gas temperatures, and power regulating means connected to the sensor means and the inhalation gas heater for controlling the amount of heat delivered by the heater such as the sensed inhalation gas temperature with respect to time is a tracking function of the sensed exhalation gas temperature and wherein the inhalation gas temperature normally tracks below the exhalation track temperature, the improvement residing in means for measuring body core temperature, and logic means connected to the body core temperature measuring means for comparing the measured body core temperature to a body core temperature threshold level and controlling the power regulating means to automatically change said tracking function in response to deviation of the body core temperature from said threshold level such that said sensed inhalation gas temperature tracks above said sensed exhalation gas temperature when said measured body core temperature is below said threshold level thereby restoring said measured body core temperature to said threshold level.

2. The system as defined in claim 1 wherein said change in the tracking function is reflected by switching of the output of the heater between inhalation gas temperature levels tracking below and above the exhalation temperature.

3. The system as defined in claim 2 including adjustable means for establishing different temperature separation between the inhalation and exhalation temperatures during said tracking below and above the exhalation temperature.

4. The system as defined in claim 1 wherein said logic means includes signal control means connected to the body core temperature measuring means for generating switching signals in response to deviation of the body core temperature from said threshold level, and relay means connected to said power regulating means for changing output levels of the heater in response to said switching signals.

5. The system as defined in claim 4 including means for separately adjusting the output levels between which the heater is switched by the relay means.

6. In a method of delivering heat to a patient by heating inhalation gas delivered to said patient and measuring the temperatures of the gas inhaled and exhaled by the patient to control the inhalation gas temperature of the heated inhaled gas such that the inhalation gas temperature with respect to time is a tracking function of the exhalation gas temperature, the improvement residing in the steps of measuring the body core temperature of the patient during said heating and delivery of the inhalation gas to the patient to detect any malfunctioning of the body temperature regulating system of the patient; normally varying the temperature of the delivered inhalation gas by an amount causing the measured inhalation gas temperature to track below the measured exhalation gas temperature during proper functioning of the body temperature regulating system; and changing said variation of the temperature of the delivered inhalation gas in response to a malfunction detection in the measurement of body core temperature such that the inhalation gas temperature tracks above the exhalation gas temperature until said detected malfunction is corrected.

7. The method as defined in claim 6 including the step of: adjusting the heat respectively delivered when tracking below and above the exhalation gas temperature by different substantially constant amounts.

8. The method as defined in claim 7 wherein the inhalation gas temperature tracks below and above the exhalation gas temperature by approximately 1° C. and 3° C., respectively.

* * * * *